(12) United States Patent
Kevwitch et al.

(10) Patent No.: US 7,678,419 B2
(45) Date of Patent: Mar. 16, 2010

(54) FORMATION OF CATALYTIC REGIONS WITHIN POROUS STRUCTURES USING SUPERCRITICAL PHASE PROCESSING

(75) Inventors: Rob Kevwitch, Chandler, AZ (US); Maximilian A. Biberger, Scottsdale, AZ (US)

(73) Assignee: SDC Materials, Inc., Tempe, AZ (US)

( * ) Notice: Subject to any disclaimer, the term of this patent is extended or adjusted under 35 U.S.C. 154(b) by 0 days.

(21) Appl. No.: 12/151,932

(22) Filed: May 8, 2008

(65) Prior Publication Data

US 2008/0280049 A1 Nov. 13, 2008

Related U.S. Application Data

(60) Provisional application No. 60/928,946, filed on May 11, 2007.

(51) Int. Cl.
*B05D 5/00* (2006.01)
(52) U.S. Cl. .................. 427/243; 427/244; 427/245
(58) Field of Classification Search .................. None
See application file for complete search history.

(56) References Cited

U.S. PATENT DOCUMENTS

| | | | |
|---|---|---|---|
| 2,419,042 A | 4/1947 | Todd | 202/205 |
| 2,519,531 A | 8/1950 | Worn | 230/95 |
| 2,689,780 A | 9/1954 | Rice | 23/106 |
| 3,001,402 A | 9/1961 | Koblin | 73/421.5 |
| 3,457,788 A | 7/1969 | Miyajima | 73/422 |
| 3,537,513 A | 11/1970 | Austin et al. | 165/70 |
| 3,741,001 A | 6/1973 | Fletcher et al. | 73/28 |
| 3,774,442 A | 11/1973 | Gustavsson | 73/28 |
| 3,959,420 A | 5/1976 | Geddes et al. | 261/112 |
| 4,008,620 A | 2/1977 | Narato et al. | 73/421.5 A |

(Continued)

FOREIGN PATENT DOCUMENTS

| JP | 56-146804 | 11/1981 |
|---|---|---|
| WO | WO 02/092503 A1 | 11/2002 |
| WO | WO 2006/079213 A1 | 8/2006 |

OTHER PUBLICATIONS

J. Heberlein, "New Approaches in Thermal Plasma Technology", Pure Appl. Chem., vol. 74, No. 3, 2002, pp. 327-335.

(Continued)

*Primary Examiner*—Shamim Ahmed
(74) *Attorney, Agent, or Firm*—Haverstock & Owens LLP (57) ABSTRACT

A method of forming a catalytic region on a porous structure having an exterior surface and a plurality of pores, the method comprising: forming a supercritical dispersion, wherein the supercritical dispersion comprises a plurality of particles dispersed in a supercritical fluid; exposing the porous structure to the supercritical dispersion; and depositing the plurality of particles from the supercritical dispersion onto the porous structure, wherein each one of the deposited plurality of particles is catalytic, thereby forming one or more catalytic regions on the porous structure. The method is particularly well suited for creating catalytic regions within pre-formed microporous structures.

25 Claims, 4 Drawing Sheets

U.S. PATENT DOCUMENTS

| | | | |
|---|---|---|---|
| 4,436,075 A | 3/1984 | Campbell et al. | 123/557 |
| 4,824,624 A | 4/1989 | Palicka et al. | 264/67 |
| 4,983,555 A | 1/1991 | Roy et al. | 501/120 |
| 4,987,033 A | 1/1991 | Abkowitz et al. | 428/469 |
| 5,043,548 A | 8/1991 | Whitney et al. | 219/121.84 |
| 5,073,193 A | 12/1991 | Chaklader et al. | 75/346 |
| 5,369,241 A | 11/1994 | Taylor et al. | 219/121.47 |
| 5,371,049 A | 12/1994 | Moffett et al. | 501/89 |
| 5,372,629 A | 12/1994 | Anderson et al. | 75/332 |
| 5,392,797 A | 2/1995 | Welch | 134/108 |
| 5,485,941 A | 1/1996 | Guyomard et al. | 222/1 |
| 5,553,507 A | 9/1996 | Basch et al. | 73/863.01 |
| 5,611,896 A | 3/1997 | Swanepoel et al. | 204/169 |
| 5,630,322 A | 5/1997 | Heilmann et al. | 62/95 |
| 5,749,938 A | 5/1998 | Coombs | 75/332 |
| 5,776,359 A | 7/1998 | Schultz et al. | 252/62.51 |
| 5,788,738 A | 8/1998 | Pirzada et al. | 75/331 |
| 5,811,187 A | 9/1998 | Anderson et al. | 428/403 |
| 5,853,815 A | 12/1998 | Muehlberger | 427/446 |
| 5,905,000 A | 5/1999 | Yadav et al. | 429/33 |
| 5,935,293 A | 8/1999 | Detering et al. | 75/10.29 |
| 5,989,648 A | 11/1999 | Phillips | 427/456 |
| 5,993,967 A | 11/1999 | Brotzman, Jr. et al. | 428/407 |
| 5,993,988 A | 11/1999 | Ohara et al. | 429/40 |
| 6,012,647 A | 1/2000 | Ruta et al. | 239/132.1 |
| 6,033,781 A | 3/2000 | Brotzman, Jr. et al. | 428/405 |
| 6,059,853 A | 5/2000 | Coombs | 75/332 |
| 6,102,106 A | 8/2000 | Manning et al. | 165/76 |
| 6,214,195 B1 | 4/2001 | Yadav et al. | 205/334 |
| 6,228,904 B1 | 5/2001 | Yadav et al. | 523/210 |
| 6,254,940 B1 | 7/2001 | Pratsinis et al. | 427/562 |
| 6,261,484 B1 | 7/2001 | Phillips et al. | 264/5 |
| 6,267,864 B1 | 7/2001 | Yadav et al. | 205/341 |
| 6,344,271 B1 | 2/2002 | Yadav et al. | 428/402 |
| 6,379,419 B1 | 4/2002 | Celik et al. | 75/346 |
| 6,387,560 B1 | 5/2002 | Yadav et al. | 429/45 |
| 6,395,214 B1 | 5/2002 | Kear et al. | 264/434 |
| 6,398,843 B1 | 6/2002 | Tarrant | 75/249 |
| 6,409,851 B1 | 6/2002 | Sethuram et al. | 148/565 |
| 6,416,818 B1 | 7/2002 | Aikens et al. | 427/383.1 |
| RE37,853 E | 9/2002 | Detering et al. | 75/10.19 |
| 6,444,009 B1 | 9/2002 | Liu et al. | 75/332 |
| 6,517,800 B1 | 2/2003 | Cheng et al. | 423/447.1 |
| 6,524,662 B2 | 2/2003 | Jang et al. | 427/535 |
| 6,531,704 B2 | 3/2003 | Yadav et al. | 250/493.1 |
| 6,554,609 B2 | 4/2003 | Yadav et al. | 432/9 |
| 6,562,495 B2 | 5/2003 | Yadav et al. | 429/12 |
| 6,569,397 B1 | 5/2003 | Yadav et al. | 423/345 |
| 6,569,518 B2 | 5/2003 | Yadav et al. | 428/323 |
| 6,572,672 B2 | 6/2003 | Yadav et al. | 75/343 |
| 6,607,821 B2 | 8/2003 | Yadav et al. | 428/323 |
| 6,610,355 B2 | 8/2003 | Yadav et al. | 427/115 |
| 6,635,357 B2 | 10/2003 | Moxson et al. | 428/548 |
| 6,641,775 B2 | 11/2003 | Vigliotti et al. | 264/618 |
| 6,652,822 B2 | 11/2003 | Phillips et al. | 423/290 |
| 6,652,967 B2 | 11/2003 | Yadav et al. | 428/403 |
| 6,669,823 B1 | 12/2003 | Sarkas et al. | 204/164 |
| 6,682,002 B2 | 1/2004 | Kyotani | 239/318 |
| 6,689,192 B1 | 2/2004 | Phillips et al. | 75/342 |
| 6,699,398 B1 | 3/2004 | Kim | 216/55 |
| 6,706,097 B2 | 3/2004 | Zornes | 96/153 |
| 6,713,176 B2 | 3/2004 | Yadav et al. | 428/402 |
| 6,716,525 B1 | 4/2004 | Yadav et al. | 428/402 |
| 6,746,791 B2 | 6/2004 | Yadav et al. | 429/30 |
| 6,772,584 B2 | 8/2004 | Chun et al. | 60/275 |
| 6,786,950 B2 | 9/2004 | Yadav et al. | 75/346 |
| 6,813,931 B2 | 11/2004 | Yadav et al. | 73/31.05 |
| 6,817,388 B2 | 11/2004 | Tsangaris et al. | 141/82 |
| 6,832,735 B2 | 12/2004 | Yadav et al. | 241/16 |
| 6,838,072 B1 | 1/2005 | Kong et al. | 423/594.2 |
| 6,855,426 B2 | 2/2005 | Yadav | 428/403 |
| 6,855,749 B1 | 2/2005 | Yadav et al. | 523/105 |
| 6,886,545 B1 | 5/2005 | Holm | 123/568.21 |
| 6,896,958 B1 | 5/2005 | Cayton et al. | 428/323 |
| 6,902,699 B2 | 6/2005 | Fritzemeier et al. | 419/38 |
| 6,916,872 B2 | 7/2005 | Yadav et al. | 524/430 |
| 6,919,527 B2 | 7/2005 | Boulos et al. | 219/121.52 |
| 6,933,331 B2 | 8/2005 | Yadav et al. | 523/210 |
| 6,986,877 B2 | 1/2006 | Takikawa et al. | 423/447.3 |
| 6,994,837 B2 | 2/2006 | Boulos et al. | 423/613 |
| 7,007,872 B2 | 3/2006 | Yadav et al. | 241/1 |
| 7,052,777 B2 | 5/2006 | Brotzman, Jr. et al. | 428/570 |
| 7,073,559 B2 | 7/2006 | O'Larey et al. | 164/76.1 |
| 7,081,267 B2 | 7/2006 | Yadav | 427/115 |
| 7,101,819 B2 | 9/2006 | Rosenflanz et al. | 501/10 |
| 7,147,544 B2 | 12/2006 | Rosenflanz | 451/28 |
| 7,147,894 B2 | 12/2006 | Zhou et al. | 427/256 |
| 7,166,198 B2 | 1/2007 | Van Der Walt et al. | 204/165 |
| 7,166,663 B2 | 1/2007 | Cayton et al. | 524/430 |
| 7,172,649 B2 | 2/2007 | Conrad et al. | 106/35 |
| 7,178,747 B2 | 2/2007 | Yadav et al. | 241/23 |
| 7,208,126 B2 | 4/2007 | Musick et al. | 423/69 |
| 7,211,236 B2 | 5/2007 | Stark et al. | 423/592.1 |
| 7,217,407 B2 | 5/2007 | Zhang | 423/610 |
| 7,307,195 B2 | 12/2007 | Polverejan et al. | 585/443 |
| 7,323,655 B2 | 1/2008 | Kim | 219/121.43 |
| 7,384,447 B2 | 6/2008 | Kodas et al. | 75/332 |
| 2002/0079620 A1 | 6/2002 | DuBuis et al. | 264/328.14 |
| 2003/0036786 A1 | 2/2003 | Duren et al. | 607/96 |
| 2003/0066800 A1* | 4/2003 | Saim et al. | 210/634 |
| 2003/0108459 A1 | 6/2003 | Wu et al. | 422/186.04 |
| 2003/0223546 A1 | 12/2003 | McGregor et al. | 378/143 |
| 2004/0023453 A1* | 2/2004 | Xu et al. | 438/202 |
| 2004/0103751 A1 | 6/2004 | Joseph et al. | 75/10.19 |
| 2004/0167009 A1 | 8/2004 | Kuntz et al. | 501/95.2 |
| 2004/0251017 A1 | 12/2004 | Pillion et al. | 165/289 |
| 2005/0000321 A1 | 1/2005 | O'Larey et al. | 75/952 |
| 2005/0000950 A1 | 1/2005 | Schroder et al. | 219/121.59 |
| 2005/0077034 A1 | 4/2005 | King | 165/163 |
| 2005/0097988 A1 | 5/2005 | Kodas et al. | 75/332 |
| 2005/0233380 A1 | 10/2005 | Pesiri et al. | 435/7.1 |
| 2005/0240069 A1 | 10/2005 | Polverejan et al. | 585/444 |
| 2005/0258766 A1 | 11/2005 | Kim | 315/111.21 |
| 2006/0051505 A1 | 3/2006 | Kortshagen et al. | 427/212 |
| 2006/0096393 A1 | 5/2006 | Pesiri | 73/863.21 |
| 2006/0105910 A1 | 5/2006 | Zhou et al. | |
| 2006/0108332 A1 | 5/2006 | Belashchenko | 219/121.47 |
| 2006/0108459 A1 | 5/2006 | De La Veaux et al. | 422/151 |
| 2006/0231525 A1 | 10/2006 | Asakawa et al. | 216/56 |
| 2007/0063364 A1 | 3/2007 | Hsiao et al. | 264/5 |
| 2007/0084308 A1 | 4/2007 | Nakamura et al. | 75/346 |
| 2007/0084834 A1 | 4/2007 | Hanus et al. | 219/121.5 |
| 2007/0087934 A1 | 4/2007 | Martens et al. | 502/214 |
| 2007/0173403 A1* | 7/2007 | Koike et al. | 502/300 |

OTHER PUBLICATIONS

T. Yoshida, "The Future of Thermal Plasma Processing for Coating", Pure & Appl. Chem., vol. 66, No. 6, 1994 pp. 1223-1230.

A. Gutsch et al., "Gas-Phase Production of Nanoparticles", Kona No. 20, 2002, pp. 24-37.

Dr. Heike Mülenweg et al., "Gas-Phase Reactions—Open Up New Roads to Nanoproducts", Degussa ScienceNewsletter No. 08, 2004, pp. 12-16.

Coating Generation: Vaporization of Particles in Plasma Spraying and Splat Formation, M. Vardelle, A. Vardelle, K-I Ii, P. Fauchais, Universite de Limoges, 123 Avenue A. Thomas 87000, Limoges, F., Pure & Chem, vol. 68, No. 5, pp. 1093-1099, 1996.

H. Konrad et al., "Nanostructured Cu-Bi Alloys Prepared by Co-Evaporation in a Continuous Gas Flow," NanoStructured Materials, vol. 7, No. 6, Apr. 1996, pp. 605-610.

M. Vardelle et al., "Experimental Investigation of Powder Vaporization in Thermal Plasma Jets," Plasma Chemistry and Plasma Processing, vol. 11, No. 2, Jun. 1991, pp. 185-201.

P. Fauchais et al., "Plasma Spray: Study of the Coating Generation," Ceramics International, Elsevier, Amsterdam, NL, vol. 22, No. 4, Jan. 1996, pp. 295-303.

P. Fauchais et al., "Les Dépôts Par Plasma Thermique," Revue Generale De L'Electricitie, RGE. Paris, FR, No. 2, Jan. 1993, pp. 7-12.

P. Fauchais et al, "La Projection Par Plasma: Une Revue," Annales De Physique, vol. 14, No. 3, Jun. 1989, pp. 261-310.

* cited by examiner

FORMATION OF CATALYTIC REGIONS WITHIN POROUS STRUCTURES USING SUPERCRITICAL PHASE PROCESSING

CROSS-REFERENCE TO RELATED APPLICATIONS

The present application claims priority to co-pending U.S. Provisional Application Ser. No. 60/928,946, filed May 11, 2007, entitled "MATERIAL PRODUCTION SYSTEM AND METHOD," which is hereby incorporated by reference as if set forth herein.

FIELD OF THE INVENTION

The present invention relates to systems and methods of forming catalytic regions within porous structures. More particularly, the present invention relates to supercritical phase processing of powders to form catalytic regions within porous structures.

BACKGROUND OF THE INVENTION

Certain microporous structures can serve as valuable industrial catalysts. Several features of these structures make them particularly well suited for catalytic applications. For example, their high surface area to volume ratio provides a dense region of reactivity. Their heterogeneity with fluid reactants and products permits relatively easy recovery of the catalyst post-reaction. Furthermore, their microscopic structure provides for physical modulation of the reactants and products in addition to any chemical catalysis.

Some microporous structures, for example some molecular sieves, do not provide for chemical catalysis, but instead solely accomplish physical modulation of working fluids or solutions. Whether or not a microporous structure provides chemical catalytic functions in addition to physical structure, is also a function of the material from which the structure is made.

Most microporous structures cannot be constructed as such, but instead rely on a variety of complex chemical and mechanical formation mechanisms, including self-assembly. These mechanisms are exploited in known production methods, such as sol-gel. Unfortunately, because these production methods and formation mechanisms can operate only on materials with chemical structure, arbitrary materials cannot be formed into a selected microporous structure. Additionally, the catalytic mechanisms within microporous structures are complex and do not always directly relate to the catalytic functionality present in precursors. Thus, formation of a microporous structure capable of performing a desired catalytic function requires a suitable precursor that can chemically form the required structure while retaining a functional group capable of performing the desired catalytic function.

Figure 1:
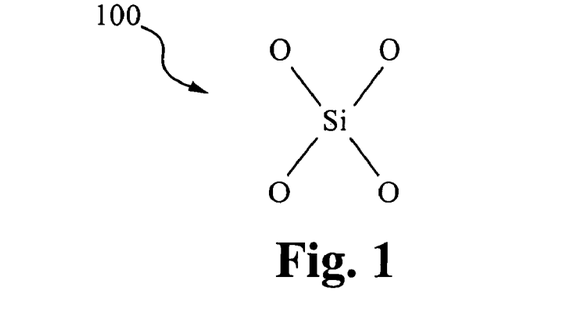
FIG. 1 illustrates the chemical structure of a precursor that, when formed into a zeolite, is suitable for use as a porous structure in accordance with the principles of the present invention.
Figure 2:
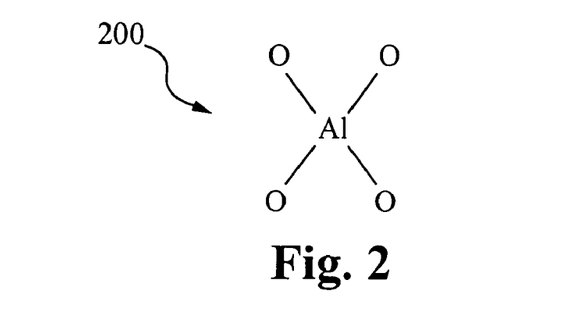
FIG. 2 illustrates the chemical structure of a precursor that, when formed into a zeolite, is suitable for use as a porous structure in accordance with the principles of the present invention.

Zeolites are a well-known class of microporous structures. Zeolites are crystalline aluminosilicate minerals that form regular, porous structures. The building blocks of zeolites have the chemical structures illustrated in FIGS. 1 and 2. Typically, a zeolite comprises $SiO_4$ structures, such as the $SiO_4$ structure 100 shown in FIG. 1, bonded with $AlO_4$ structures, such as the $AlO_4$ structure 200 shown in FIG. 2, through shared oxygen atoms. The structure shown in FIG. 2 is not stable on its own, but appears within a crystal including $SiO_4$ structures.

However, what is needed in the art is a system for and a method of engineering the catalytic behavior of a porous structure without having to rely on synthesis of precursors suitable for formation into the porous structure.

SUMMARY OF THE INVENTION

The present invention provides a system for and a method of forming catalytic regions within pre-formed porous structures. Supercritical phase processing is employed to achieve such catalytic region formation. For the purposes of this disclosure, a supercritical fluid is any fluid that is at a temperature and a pressure above its thermodynamic critical point.

In one aspect of the present invention, a method of forming a catalytic region on a porous structure is disclosed. The porous structure has an exterior surface and a plurality of pores. In the method, a supercritical dispersion is formed, wherein the supercritical dispersion comprises a plurality of particles dispersed in a supercritical fluid. The porous structure is then exposed to the supercritical dispersion. Finally, the particles from the supercritical dispersion are deposited onto the porous structure. These deposited particles are catalytic, thereby enabling the formation of one or more catalytic regions on the porous structure.

In another aspect of the present invention, a method of forming a catalytic region on a microporous structure is disclosed. The microporous structure has an exterior surface and a plurality of pores. In the method, a plurality of particles is dispersed within a carrier fluid, thereby forming a carrier mixture. A supercritical fluid is mixed with the carrier mixture, thereby forming a heterogeneous mixture. The carrier fluid is then removed from the heterogeneous mixture, thereby forming a supercritical dispersion. The supercritical dispersion comprises the plurality of particles dispersed in the supercritical fluid. The microporous structure is exposed to the supercritical dispersion. Finally, the supercritical fluid is removed from the supercritical dispersion while the supercritical dispersion is in contact with the porous structure, thereby depositing the plurality of particles from the supercritical dispersion onto the microporous structure. The deposited particles are catalytic, thereby enabling the formation of one or more catalytic regions on the porous structure.

Other aspects of the present invention relate to systems adapted to perform methods in accordance with the present invention. The present invention is particularly well-suited for use with pre-formed microporous structures. For the purposes of this disclosure, the use of the term "pre-formed" indicates that the porous structure has already been formed, with a plurality of pores disposed within the porous structure, prior to the method steps of the present invention being performed. Additionally, for the purposes of this disclosure, a microporous structure is a structure having a plurality of very fine pores. In one embodiment, a microporous structure comprises a plurality of pores having an average pore diameter of less than 1 micron. In another embodiment, the microporous structure comprises a plurality of pores having an average pore diameter of less than 2 nanometers.

DETAILED DESCRIPTION OF THE INVENTION

The description below concerns several embodiments of the invention. The discussion references the illustrated preferred embodiment. However, the scope of the present invention is not limited to either the illustrated embodiment, nor is it limited to those discussed, to the contrary, the scope should be interpreted as broadly as possible based on the language of the Claims section of this document.

This disclosure refers to both particles and powders. These two terms are equivalent, except for the caveat that a singular "powder" refers to a collection of particles. The present invention may apply to a wide variety of powders and particles.

For the purposes of this disclosure, a microporous structure is a structure having a plurality of very fine pores. In one embodiment, a microporous structure comprises a plurality of pores having an average pore diameter of less than 1 micron. In another embodiment, the microporous structure comprises a plurality of pores having an average pore diameter of less than 2 nanometers.

The present invention will be readily understood by the following detailed description in conjunction with the accompanying drawings. In order to facilitate this description, like reference numerals designate like elements.

Figure 3A:
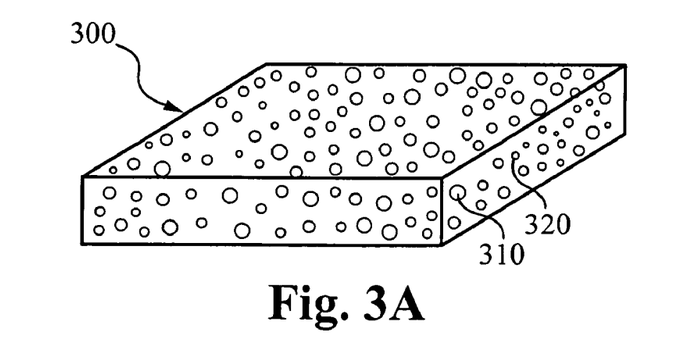
FIG. 3A is a perspective view of one embodiment of a porous structure suitable for processing in accordance with the principles of the present invention.
Figure 3B:
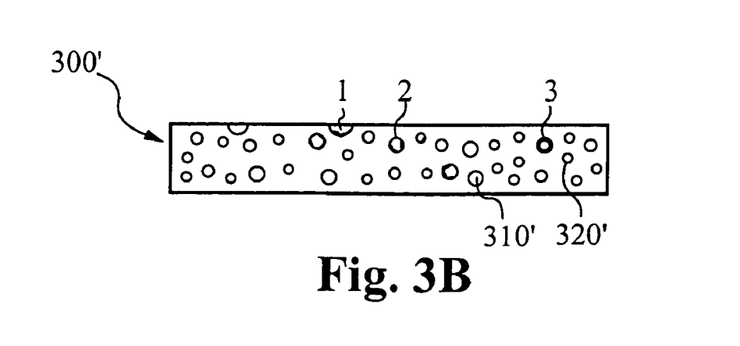
FIG. 3B is a cross-sectional side view of one embodiment of a porous structure that has been processed in accordance with the principles of the present invention.

FIGS. 3A and 3B illustrate porous structures 300 and 300'. The porous structure 300 includes a plurality of pores, e.g. 310, 320, formed therein. In a preferred embodiment, a porous structure, such structure 300, is used as an input to a process that produces a porous structure comprising a catalytic region, such as structure 300', that comprises a deposited particulate. In some embodiments, the present invention prescribes forming a catalytic region within one or more of the pores, e.g. 310, of the porous structure 300. In some embodiments, the present invention prescribes forming a catalytic region on an exterior surface of the porous structure 300. Some embodiments form catalytic regions in multiple locations of the porous structure 300.

The porous structure 300 includes pores of various sizes. Some pores, e.g. 310, are relatively large, while other pores, e.g. 320, are relatively small. Although the illustrated structure has non-uniform pore sizes, some embodiments of the present invention operate on porous structures with substantially uniform pore sizes. For example, some embodiments take zeolites as inputs.

Furthermore, the illustrated relationship between the pores 310 and 320 and the size of the porous structure 300 is not necessarily to scale. In some embodiments of the present invention, the pores 310 and 320 are very small in size compared to the porous structure 300. Preferably, porous structure 300 is a microporous structure, having a plurality of very fine pores. In one embodiment, the microporous structure 300 comprises a plurality of pores having an average pore diameter of less than 1 micron. In another embodiment, the microporous structure 300 comprises a plurality of pores having an average pore diameter of less than 2 nanometers.

The porous structure 310', shown in cross-section by FIG. 3B, includes a plurality of catalytic regions, e.g. 1, 2, 3. In the present invention, a porous structure, e.g. 300 of FIG. 3A, is taken as an input to a process that produces catalytic regions on that porous structure. In particular, some embodiments of the present invention relate to processes that form a catalytic region on a porous structure by depositing a particulate onto the porous structure.

In a preferred embodiment, a catalytic particulate is deposited onto a preformed porous structure to form a catalytic region. The particulate is catalytic prior to deposition. In some embodiments, the catalytic functions of the particulate are substantially unchanged by deposition. Preferably, the particulate is deposited in such a manner as to preserve substantially all catalytic functionality of the catalytic particulate. In other embodiments, the catalytic functions of the particulate are substantially altered by deposition. In some of these embodiments, the process of deposition alters a catalytic function of the particulate. In other embodiments, the chemical or physical environment surrounding the deposited particulate alters its catalytic function. The particulate can vary from embodiment to embodiment. In a preferred embodiment, the particulate is a nano-structured powder, or nano-powder, having an average grain size less than 250 nanometers and an aspect ratio between one and one million In some embodiments of the present invention, a porous structure contains multiple types of catalytic regions. These different types of catalytic regions can provide the same catalytic function, while being disposed in different locations. Alternatively, different types of catalytic regions can provide different types of catalytic functions. For example, some embodiments can include catalytic regions having catalytic functions that depend on their location, while other embodiments can include catalytic regions having differing functions that are not correlated with their location. It is contemplated that a single embodiment can comprise catalytic regions whose function depends on location and catalytic regions whose function is unrelated to location.

In some embodiments, depositing a single type of particulate onto a porous structure in different types of locations produces catalytic regions with differing functions. In other embodiments, depositing differing types of particulate onto different locations produces such regions.

FIG. 3B illustrates a porous structure 300' with three different types of catalytic regions. The catalytic region 1 is disposed on an exterior pore of the porous structure 300', where the pore is not completely enclosed. The catalytic region 2 is disposed to partially surround an inner channel, or interior pore, of the porous structure 300'. The catalytic region 3 is disposed to completely surround an inner channel, or interior pore, of the porous structure 300'. As stated above, some embodiments of the present invention relate to structures where the regions 1, 2, and 3 have differing catalytic functions that depend on their location. Other embodiments relate to structures where the regions 1, 2, and 3 have the same catalytic function. Still, other embodiments relate to structures where the regions 1, 2, and 3 have differing catalytic functions that do not depend on their location.

The present invention provides systems for and methods of forming these catalytic regions on a porous structure. Such systems and methods preferably include means for forming a supercritical dispersion from a supercritical fluid and a particulate. FIGS. 4A to 4F illustrate one embodiment of a system and process flow for depositing a catalytic particulate and forming a catalytic region on a porous structure using a supercritical dispersion.

Figure 4A:
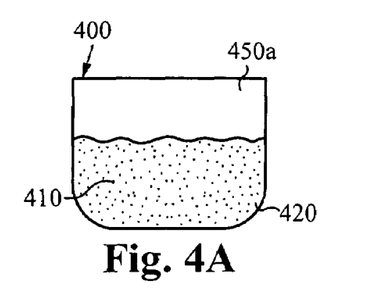
FIGS. 4A-4F illustrate one embodiment of a system and process flow for depositing a catalytic particulate and forming a catalytic region on a porous structure in accordance with the principles of the present invention.

In FIG. 4A, a chamber 400 is provided with a carrier mixture comprising a carrier fluid 420 and a particulate 410. The carrier mixture occupies a volume of the chamber 400, leaving a first void 450a within the chamber 400. In a preferred embodiment, chamber 400 can be selectively opened and closed to enable the addition, mixture, exposure, and removal of the contents, such as fluids and catalytic particles.

Figure 4B:
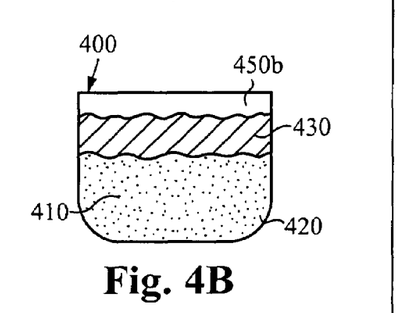

In FIG. 4B, the chamber 400 has received a supercritical fluid 430. The supercritical fluid 430 now occupies a portion of the first void 450a, leaving a second void 450b. The carrier mixture comprising the particulate 410 and the carrier fluid 420, along with the supercritical fluid 430 all occupy the remaining space in the chamber 400.

Figure 4C:
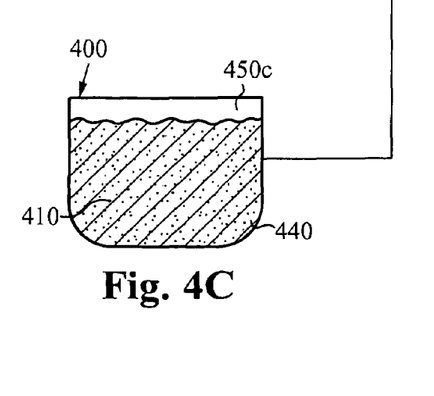

The illustrated embodiment includes means for forming a heterogeneous mixture 440 comprising a mixture of the carrier fluid 420 and the supercritical fluid 430, with the particulate 410 dispersed therein. In FIG. 4C, the supercritical fluid 430 has mixed with the carrier mixture, comprising the carrier fluid 420 and the particulate 410, to form a heterogeneous mixture 440. The heterogeneous mixture comprises the particulate 410, the carrier fluid 420 and the supercritical fluid 430 and occupies a portion of the chamber 400, leaving the third void 450c. In some embodiments, the supercritical fluid 430 and the carrier mixture mix spontaneously, while in other embodiments, energy must be provided to mix the two. In some embodiments, the third void 450c and the second void 450b have the same volume, while in other embodiments, the third void 450c is greater in volume than the second void 450b, and in other embodiments, the third void 450c is lesser in volume than the second void 450b. These volume changes are sometimes dependent on temperature changed induced by mixing or energy introduction.

Figure 4D:
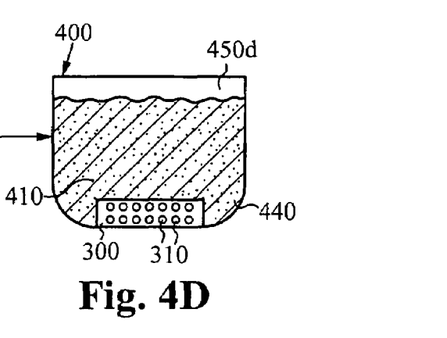

FIG. 4D illustrates a chamber 400 containing a heterogeneous mixture 440 where a porous structure 300, such as illustrated in FIG. 3A, has been introduced. The porous structure comprises a plurality of pores 310, and is preferably a microporous structure. In a preferred embodiment, the porous structure is immersed in the heterogeneous mixture 440. The combination of the heterogeneous mixture 440 and the porous structure 300 occupy a volume of the chamber 400, leaving a fourth void 450d.

Figure 4E:
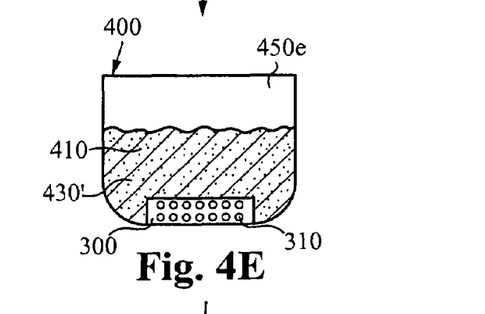

The present invention includes means for removing the carrier fluid from the heterogeneous mixture. Once the porous structure 300 has been introduced, the carrier fluid 420 is substantially removed from the heterogeneous mixture 440, thereby producing a supercritical dispersion 430' that comprises the particulate 410 and the supercritical fluid 430, as illustrated in FIG. 4E. This removal produces the fifth void 450e of increased size relative to the fourth void 450d in the chamber 400. Furthermore, the presence of both the supercritical dispersion 430' and the porous structure 300 within the chamber 400 exposes the porous structure 300 to the supercritical dispersion 430'. In some embodiments, the means for removing substantially all of the carrier fluid 420 includes a reverse osmosis device or a filtering device.

Additionally, systems for forming catalytic regions on porous structures in accordance with the present invention preferably include means for removing the supercritical fluid 430 from the supercritical dispersion 430' while the supercritical dispersion 430' is in contact with the porous structure 300. For example, in FIG. 4F, the chamber 400 is vented to a lower pressure environment, thereby producing a gas 430" from the supercritical fluid 430 of the supercritical dispersion 430'. As the supercritical fluid 430 evaporates to form the gas 430", it is substantially removed from the supercritical dispersion 430'.

Figure 4F:
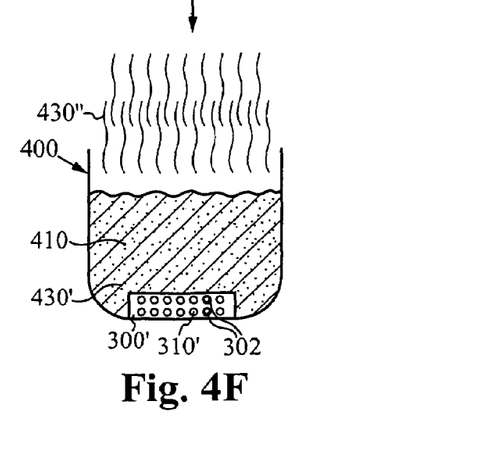

This removal increases the relative concentration of particulate 410 within the supercritical dispersion 430', resulting in deposition of the particulate 410 on porous structure 300 to form the deposited regions 302 on porous structure 300'. In FIG. 4F, the deposited regions 302 are within the pores 310. However, in some embodiments, the deposited regions are formed in or on other locations, such as on an exterior surface of a porous structure. In any case, the deposited regions are catalytic, thus forming a catalytic porous structure 300'.

In some embodiments, the deposited regions can be catalytic due in part to the surrounding environment (chemical environment, physical environment, or electrical environment) provided by the porous structure, or due in part to their inherent properties, or due in part to a combination of surrounding environment and inherent properties.

Preferably, embodiments of the present invention include means for immersing the porous structure 300 in the heterogeneous mixture 440. Such means are illustrated in FIG. 4D, where the entire porous structure 300 is immersed in the heterogeneous mixture 440. Additionally, embodiments of the present invention also include means for immersing the porous structure 300 in the supercritical dispersion 430'. Such means are illustrated in FIG. 4E, where the entire porous structure 300 is immersed in the supercritical dispersion 430'.

It is contemplated that the particular materials employed within the present invention can vary. However, in a preferred embodiment, the carrier fluid 420 is a surfactant. Furthermore, the carrier fluid 420 preferably comprises one or more of the following: water, oil, and alcohol. The particulate 410 can be a nanopowder, having an average grain size less than 250 nanometers and an aspect ratio between one and one million. The particulate 410 can be provided in other sizes as well. The porous structure 300 can be a zeolite or an alternative chemical structure.

Various methods in accordance with the present invention relate to inducing deposition of particulate from a supercritical mixture onto a porous structure.

Figure 5:
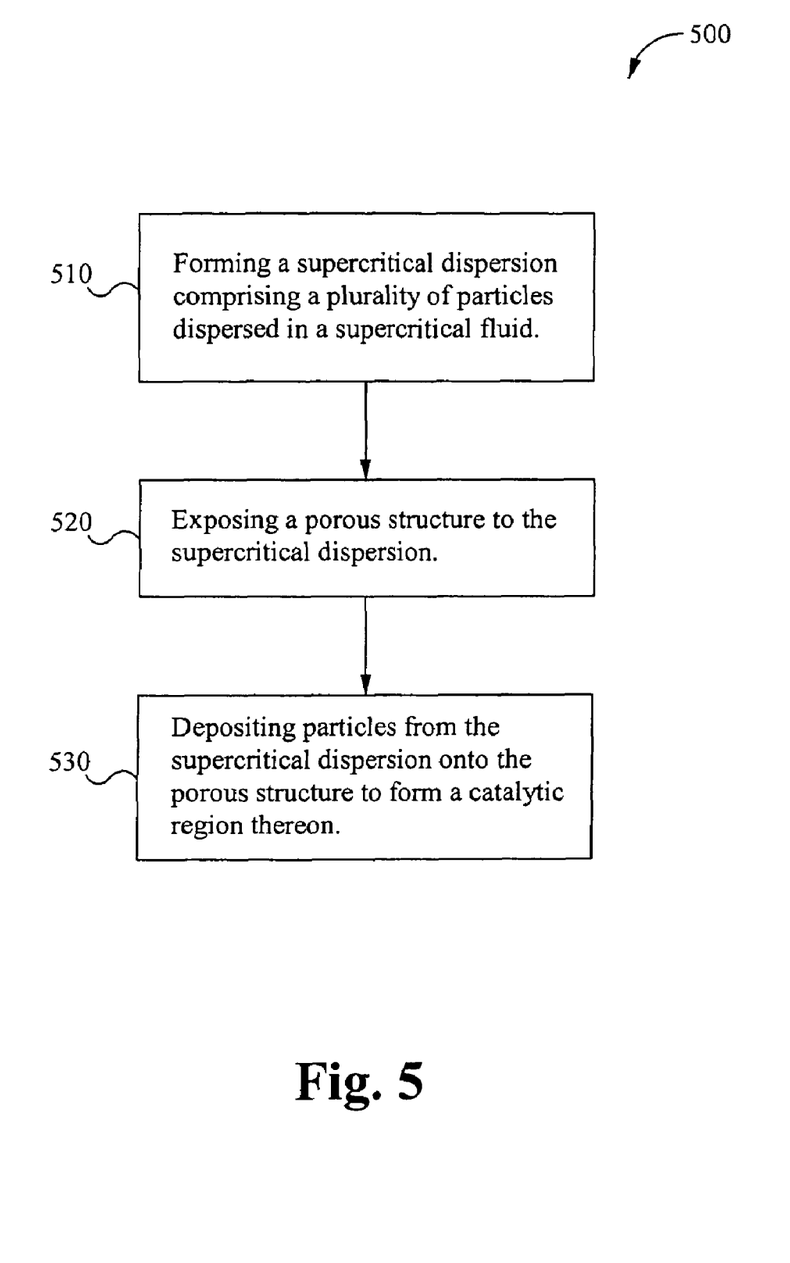
FIG. 5 is a flowchart illustrating one embodiment of a method of forming a catalytic region on a porous structure in accordance with the principles of the present invention.

FIG. 5 is a flowchart illustrating one embodiment of a method 500 of forming a catalytic region on a porous structure in accordance with the principles of the present invention.

At step 510, a supercritical dispersion is formed. The supercritical dispersion comprises a plurality of particles dispersed in a supercritical fluid. This supercritical dispersion can be formed in a variety of ways, including, but not limited to, the addition and removal of fluids and particles.

At step 520, a porous structure, having a plurality of pores, is exposed to the supercritical dispersion. Such exposure can be achieved in a variety of ways. In a preferred embodiment, the supercritical dispersion is contained within a chamber and the porous structure is immersed in the supercritical dispersion.

At step 530, the particles from the supercritical dispersion are deposited onto the porous structure, thereby forming catalytic regions on the porous structure. The particles are preferably catalytic prior to deposition. However, it is contemplated that particles can become catalytic or that their catalytic function can change in response to being deposited on the porous structure. Also, the particles can be deposited in a variety of different locations, such as on the exterior surface of the porous structure and/or on the interior surface of the pores. Such deposition can be achieved in a variety of ways. Furthermore, the catalytic regions can be formed in a variety of different locations on the porous structure, such as on the exterior surface of a pore or on the interior surface of a pore, with the catalytic region partially or completely surrounding the pore.

Figure 6:
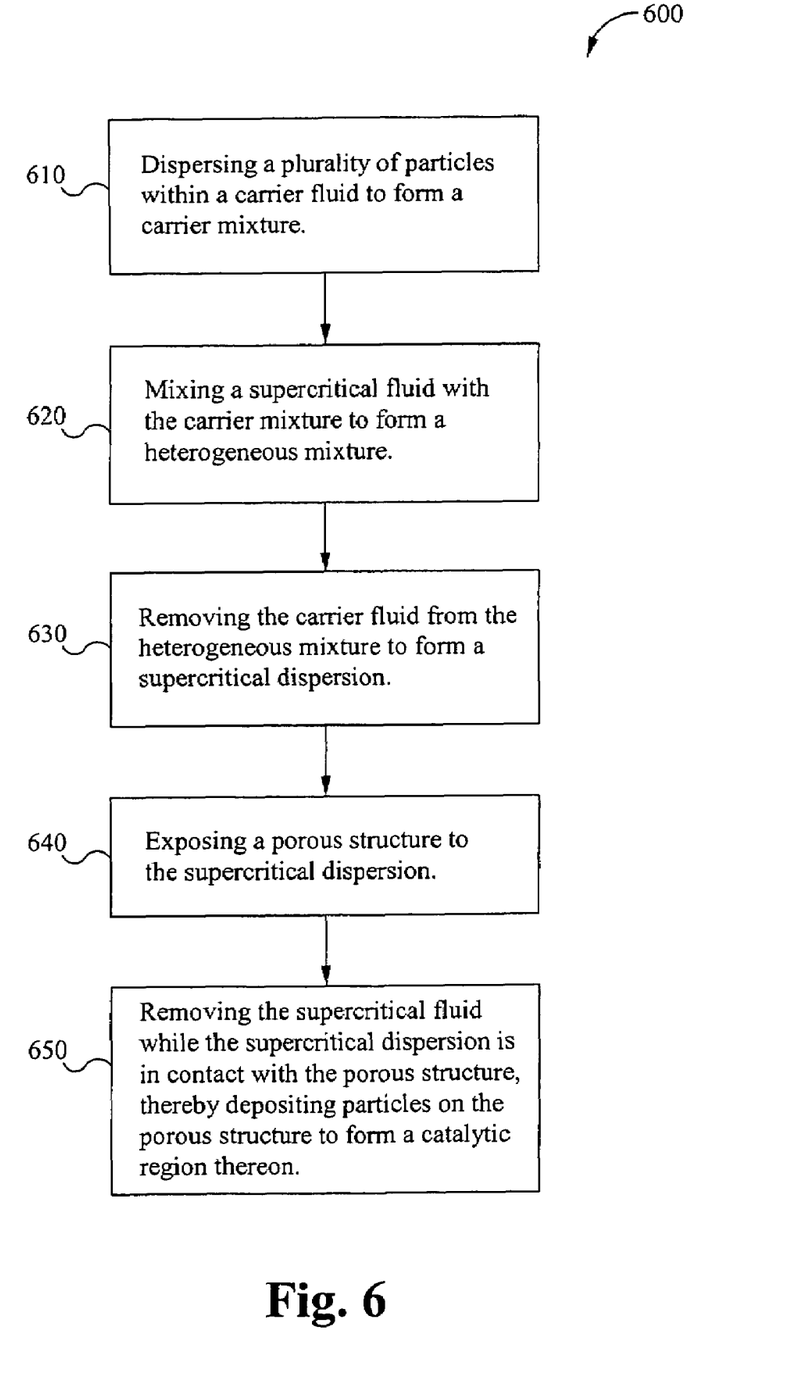
FIG. 6 is a flowchart illustrating another embodiment of a method of forming a catalytic region on a porous structure in accordance with the principles of the present invention.

FIG. 6 is a flowchart illustrating another embodiment of a method 600 of forming a catalytic region on a porous structure in accordance with the principles of the present invention. The steps of the method 600 are preferably performed using a chamber in order to hold and contain the fluids and particles.

At step 610, a plurality of particles is dispersed within a carrier fluid, thereby forming a carrier mixture. Preferably, the particles are either catalytic or predisposed to becoming catalytic once deposited onto the porous structure.

At step 620, a supercritical fluid is mixed with the carrier mixture, thereby forming a heterogeneous mixture. Accordingly, the heterogeneous mixture comprises the supercritical fluid, the carrier fluid and the plurality of particles.

At step 630, the carrier fluid is removed from the heterogeneous mixture, thereby forming a supercritical dispersion that comprises the plurality of particles dispersed within the supercritical fluid. Such removal of the carrier fluid can be achieved in a variety of ways, including, but not limited to, reverse osmosis and filtering.

At step 640, a porous structure, having a plurality of pores, is exposed to the supercritical dispersion. Such exposure can include the porous structure being immersed in the supercritical dispersion.

At step 650, the supercritical fluid is removed from the region while the supercritical dispersion is in contact with the porous structure. This removal increases the relative concentration of particles within the supercritical dispersion, thereby promoting the deposition of the particles on the porous structure. Because of the catalytic nature of the particles, their deposition on the porous structure results in the formation of catalytic regions on the porous structure. The particles can be deposited in a variety of different locations on the porous structure. Similarly, the catalytic regions can be formed in a variety of different location on the porous structure.

The present invention provides methods and systems that provide for formation of catalytic regions on porous structures. The present invention uses an already-formed porous structure as a substrate, upon which catalytic particles are deposited to form catalytic regions. In some embodiments, the catalytic particles retain their functionality following deposition onto the substrate porous structure. Hence, the catalytic behavior of the porous structure can be engineered without relying on synthesis of precursors suitable for formation into porous structures.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A method of forming a catalytic region on a pre-formed porous structure having an exterior surface and a plurality of pores, the method comprising:
    forming a supercritical dispersion, wherein the supercritical dispersion comprises a plurality of particles dispersed in a supercritical fluid;
    exposing the pre-formed porous structure to the supercritical dispersion; and
    depositing the plurality of particles from the supercritical dispersion onto the porous structure, wherein each one of the deposited plurality of particles is catalytic, thereby forming one or more catalytic regions on the porous structure.

2. The method of claim 1, wherein the porous structure is a microporous structure.

3. The method of claim 2, wherein the plurality of pores has an average pore diameter of less than 1 micron.

4. The method of claim 2, wherein the plurality of pores has an average pore diameter of less than 2 nanometers.

5. The method of claim 2, wherein the plurality of particles is a nano-powder having an average grain size less than 250 nanometers and an aspect ratio between one and one million.

6. The method of claim 1, wherein one or more of the catalytic regions is formed to partially or completely surround an interior pore within the porous structure.

7. The method of claim 1, wherein each one of the plurality of particles is catalytic prior to its deposition onto the porous structure.

8. The method of claim 1, wherein the step of forming the supercritical dispersion comprises:
    dispersing the plurality of particles within a carrier fluid, thereby forming a carrier mixture;
    mixing the supercritical fluid with the carrier mixture, thereby forming a heterogeneous mixture; and
    removing the carrier fluid from the heterogeneous mixture, thereby forming the supercritical dispersion.

9. The method of claim 8, wherein the carrier fluid is a surfactant.

10. The method of claim 8, wherein the carrier fluid comprises a fluid selected from the group consisting of water, oil and alcohol.

11. The method of claim 8, wherein the step of removing the carrier fluid from the heterogeneous mixture comprises performing reverse osmosis.

12. The method of claim 8, wherein the step of removing the carrier fluid from the heterogeneous mixture comprises a filtering process.

13. The method of claim 1, wherein the step of depositing the plurality of particles onto the porous structure comprises removing the supercritical fluid from the supercritical dispersion while the supercritical dispersion is in contact with the porous structure.

14. The method of claim 13, wherein the step of removing the supercritical fluid from the supercritical dispersion comprises:
    exposing the supercritical dispersion to a low-pressure environment; and
    venting the supercritical fluid to the low-pressure environment.

15. A method of forming a catalytic region on a pre-formed microporous structure having an exterior surface and a plurality of pores, the method comprising:
    dispersing a plurality of particles within a carrier fluid, thereby forming a carrier mixture;
    mixing a supercritical fluid with the carrier mixture, thereby forming a heterogeneous mixture;
    removing the carrier fluid from the heterogeneous mixture, thereby forming a supercritical dispersion, wherein the supercritical dispersion comprises the plurality of particles dispersed in the supercritical fluid;
    exposing the pre-formed microporous structure to the supercritical dispersion; and
    removing the supercritical fluid from the supercritical dispersion while the supercritical dispersion is in contact with the porous structure, thereby depositing the plurality of particles from the supercritical dispersion onto the microporous structure, wherein each one of the deposited plurality of particles is catalytic, and the deposition of the particles forms one or more catalytic regions on the microporous structure.

16. The method of claim 15, wherein the plurality of pores has an average pore diameter of less than 1 micron.

17. The method of claim 15, wherein the plurality of pores has an average pore diameter of less than 2 nanometers.

18. The method of claim 15, wherein the plurality of particles is a nano-powder having an average grain size less than 250 nanometers and an aspect ratio between one and one million.

19. The method of claim 15, wherein one or more of the catalytic regions is formed to partially or completely surround an interior pore within the microporous structure.

20. The method of claim 15, wherein each one of the plurality of particles is catalytic prior to its deposition onto the porous structure.

21. The method of claim 15, wherein the carrier fluid is a surfactant.

22. The method of claim 15, wherein the carrier fluid comprises a fluid selected from the group consisting of water, oil and alcohol.

23. The method of claim 15, wherein the step of removing the carrier fluid from the heterogeneous mixture comprises performing reverse osmosis.

24. The method of claim 15, wherein the step of removing the carrier fluid from the heterogeneous mixture comprises a filtering process.

25. The method of claim 15, wherein the step of removing the supercritical fluid from the supercritical dispersion comprises:

exposing the supercritical dispersion to a low-pressure environment; and venting the supercritical fluid to the low-pressure environment.

* * * * *